(12) United States Patent
Nakajima

(10) Patent No.: US 6,355,036 B1
(45) Date of Patent: Mar. 12, 2002

(54) BONE ADJUSTER

(75) Inventor: Hideo Nakajima, Tokyo (JP)

(73) Assignee: Kyowa Precision Instruments Corp., Ichikawa (JP)

( * ) Notice: Subject to any disclaimer, the term of this patent is extended or adjusted under 35 U.S.C. 154(b) by 0 days.

(21) Appl. No.: 09/570,428

(22) Filed: May 12, 2000

(30) Foreign Application Priority Data

Aug. 2, 1999 (JP) ............................................. 11-218557

(51) Int. Cl.$^7$ ............................................... A61B 17/56
(52) U.S. Cl. .............................. 606/57; 606/59; 606/54; 606/71
(58) Field of Search .............................. 606/57, 59, 54, 606/55, 56, 58, 60, 105, 69, 71

(56) References Cited

U.S. PATENT DOCUMENTS

| | | | |
|---|---|---|---|
| 4,696,293 A | * 9/1987 | Ciullo | 606/57 |
| 5,630,815 A | * 5/1997 | Pohl et al. | 606/59 |
| 5,891,144 A | * 4/1999 | Mata et al. | 606/59 |
| 5,902,304 A | * 5/1999 | Walker et al. | 606/71 |
| 6,053,915 A | * 4/2000 | Bruchmann | 606/54 |
| 6,187,004 B1 | * 2/2001 | Fearon | 606/57 |

FOREIGN PATENT DOCUMENTS

JP          A-10-43203          2/1998

* cited by examiner

*Primary Examiner*—Pedro Philogene
(74) *Attorney, Agent, or Firm*—Oliff & Berridge, PLC

(57) ABSTRACT

A bone adjuster 20 has a first lift plate 22 to be fastened to one of two opposed bone fragments to be adjusted, a second lift plate 24 to be fastened to the other bone fragment and an adjusting shaft 26 which is extended between both the lift plates 22 and 24 to adjust a space between the fragments. The first lift plate 22 comprises a mounting plate 28 and a screw-in connecting portion 34 which is connected with the mounting plate 28 via a hinge 36 and in which the adjusting shaft 26 is screwed to be supported. The second lift plate 24 also comprises a mounting plate 42 and a catching portion 48 which is rotatably fixed to the mounting plate 42 via a hinge 46 to catch the leading end of the adjusting shaft 26. The screw-in connecting portion 34 and the catching portion 48 are supported on the mounting plates 28 and 42 at a desired angle by the hinges 36 and 46, so that the mounting plates 28, 42 can be installed parallel to each other even when the bone fragments are skewed so as to appropriately hold the adjusting shaft 26.

18 Claims, 8 Drawing Sheets

BONE ADJUSTER

BACKGROUND OF THE INVENTION

The present invention relates to a bone adjuster for increasing or decreasing a space between two opposed bone fragments.

The treatment of inherent deformities or other bone abnormalities using bone lengthening techniques has become more common. For example, such a bone lengthening technique may be employed to mechanically expand a space between bone fragments to allow new bone to grow from the opposed ends of the bone fragments, thereby lengthening or correcting another deformity in the bone.

Various instruments have been developed to facilitate bone lengthening techniques, such as those disclosed, for example, in Japanese Patent Application Laid-Open Publication No. Hei 10-43203.

FIG. 12 shows one conventional bone lengthening instrument. When this conventional bone lengthening instrument is used for distraction of bone fragments, plates 10 and 12 are fastened to the opposed bone fragments and a shaft 14 is screwed through the plate 10 so to have its leading end engaged with the plate 12. This shaft 14 is operated to widen the space between the plates 10 and 12. This increased space between the bone fragments promotes osteogenesis.

This conventional bone lengthening instrument can enlarge the space between the opposed bone fragments, but the direction of enlargement is strictly linear. Therefore, the bone lengthening is limited to filling a linearly enlarged space between bone fragments.

Bone deformities are sometimes caused on a part of skeletal frame having curved portions such as skull, jaw, and face areas, most particularly cheekbones and the skull. When conventional bone lengthening instruments are used to adjust the bone of such a swelled skeletal frame, the bone is formed linearly as described above. It is difficult, or impossible, to form the bone so to have a natural shape along a peripheral skeletal frame having a bulbous portion.

SUMMARY OF THE INVENTION

The present invention was achieved in view of the circumstances described above. It is an object of the invention to provide a bone adjuster capable of adjusting any bones in conformity with their shape, including swelled skeletal frame and a linear skeletal frame bones.

To achieve the above object, the present invention is directed to a bone adjuster comprising a first lift plate to be fastened to one of two opposed bone fragments, a second lift plate to be fastened to the other fragment, and an adjusting shaft which is screwed through the first lift plate and has its leading end engaged with the second lift plate. The adjusting shaft is rotated to adjust a distance between the lift plates so as to adjust a space between the opposed bone fragments. The first lift plate is provided with a first mounting plate to be fastened to one of the bone fragments and a screw-in connecting portion which is connected to the first mounting plate and in which the adjusting shaft is screwed; the second lift plate is provided with a second mounting plate to be fastened to the other bone fragment and a catching portion which is connected to the second mounting plate and holds the leading end of the adjusting shaft; and at least the catching portion is connected to the second mounting plate via a hinge.

In a device of the above configuration, the adjusting shaft is extended between the screw-in connecting portion of the first lift plate and the catching portion of the second lift plate and rotated to increase or decrease the space between both the plates so to adjust the space between the bone fragments. The bone adjuster of the invention can linearly adjust the space between the bone fragments and can also adjust a bone in conformity with its skeletal frame, even when the bone fragment to be adjusted has a curved or bulbous portion, because at least the catching portion is pivotally connected to the second mounting plate for supporting it via the hinge.

Specifically, when this bone adjuster is used to adjust a skeletal frame having a bulbous portion, the catching portion is pivoted via the hinge and supported by the second mounting plate at an angle corresponding to the skeletal frame, so that the space between the bone fragments can be expanded to rise up along the peripheral skeletal frame or decreased to become low.

The invention may be configured so that both the screw-in connecting portion and the catching portion of the aforesaid invention pivotably connected to the first mounting plate and the second mounting plate via a hinge respectively.

As described above, both the screw-in connecting portion and the catching portion are connected to the first mounting plate and the second mounting plate via the hinge respectively, so that bone fragments of a largely bulbous bone, such as a skull, can also be adjusted appropriately. Specifically, the screw-in connecting portion and the catching portion are respectively pivoted via the hinge and supported by the mounting plate at an angle corresponding to the skeletal frame, so that, even when a skeletal frame had a sharp degree of curvature, the space between the bone fragments can be expanded to largely rise or be decreased to become low in conformity with its shape.

The bone adjuster of the present invention may also be configure to have a stopping flange formed on the end portion of the adjusting shaft of the aforesaid invention so as to externally protrude from its outer periphery, wherein the catching portion comprises a catching plate having a catching surface to engage with the stopping flange and the catching plate is formed a holding hole in which the end of the adjusting shaft is inserted and held.

By forming the holding hole in the catching plate and the stopping flange on the adjusting shaft, a single type of bone adjuster can be used to increase and to decrease the space between the bone fragments. For example, when the space between the bone fragments is to be expanded, the stopping flange is engaged with the inside catching surface on the opposed side of the screw-in connecting portion of the catching plate, and the adjusting shaft is rotated in this state to enable expansion of the catching plate. On the other hand, to pull the catching plate, the stopping flange is engaged with the outside catching surface of the catching plate, and the adjusting shaft is rotated in this state to.

DETAILED DESCRIPTION OF THE PRESENT INVENTION

Figure 1:
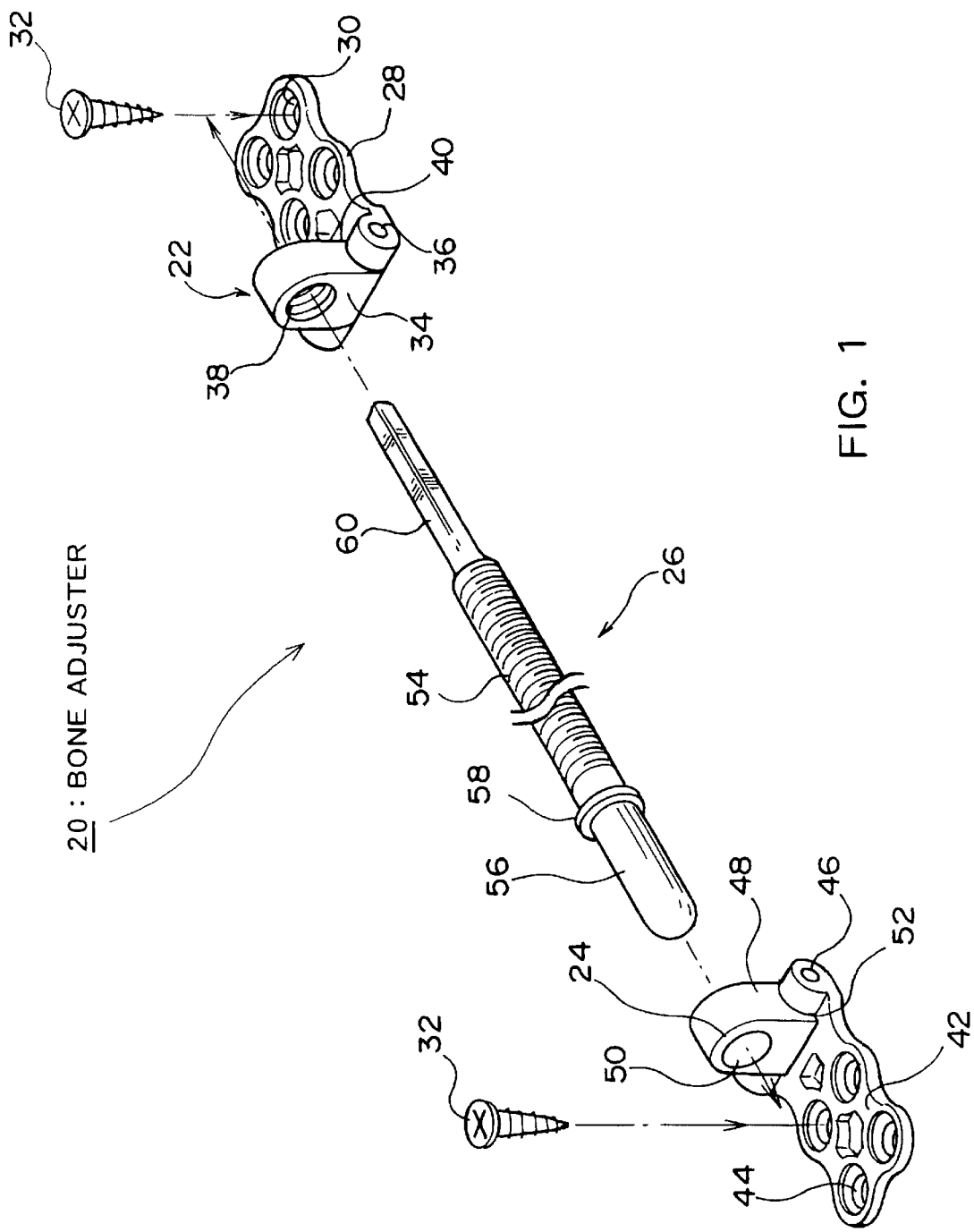
FIG. 1 is an expansion diagram of a bone adjuster according to a first embodiment of the invention.

Preferred embodiments of the present invention will be described with reference to the accompanying drawings.
First Embodiment FIG. 1 shows a structure of a bone adjuster according to a first embodiment. In FIG. 1, a bone adjuster 20 is provided with a first lift plate 22 attached to one of opposed bone fragments to be adjusted and a second lift plate 24 attached to the other. The bone adjuster 20 is also provided with an adjusting shaft 26 which is extended through the lift plates 22 and 24 to increase or decrease a distance between them. The above component parts of the bone adjuster 20 will be described in detail below.

These members of the bone adjuster 20 are made of a material such as titanium with a little influence on the human body because they are implanted in the human body for a predetermined period.

The first lift plate 22 has a mounting plate 28 for attaching the plate 22 to a bone fragment. The mounting plate 28 has a plurality of bolt holes 30 formed to insert fixing bolts 32 therethrough.

The first lift plate 22 also has a screw-in connecting portion 34 which has a screw hole for accepting the adjusting shaft 26. The screw-in connecting portion 34 is connected to the mounting plate 28 via a hinge 36 so to conform with various shapes of the skeletal frame to be adjusted, so that it is pivotable with the hinge 36 as an axis, enabling support of the adjusting shaft 26 at an appropriate angle.

The screw-in connecting portion 34 is formed of a stopper 40 which limits a pivotable angle of the screw-in connecting portion 34 to within a predetermined range. Specifically, the screw-in connecting portion 34 is rotatably connected to the mounting plate 28 with the hinge 36 as an axis, but has its pivotable range limited by the stopper 40 in order to stand upright on the mounting plate 28. For example, pivoting of the screw-in connecting portion 34 in a direction (i.e., backward) to approach the mounting plate 28 is limited by the stopper 40. Therefore, workability is maintained because the screw-in connecting portion 34 can be kept in the upright position on the mounting plate 28 when the adjusting shaft 26 is inserted into it.

On the other hand, the second lift plate 24 has substantially the same structure as the first lift plate and is provided with a mounting plate 42 used for fastening to the bone fragment. The mounting plate 42 is formed a plurality of bolt holes 44 for fastening to the bone fragment. The bolts 32 are inserted into the bolt holes 44 to fasten the mounting plate 42 to the bone fragment.

The mounting plate 42 is provided with a board-shaped catching portion 48 having a catching hole 50 for catching an end portion of the adjusting shaft 26. The catching portion 48 is provided with two catching faces 48a, 48b. To increase the space between the bone fragments, the end of the adjusting shaft 26 is inserted into the inner catching face 48a to engage a stopping flange 58 of the adjusting shaft 26 with the catching face 48a. To decrease the space between the bone fragments, the adjusting shaft 26 is inserted from the outer catching face 48b to engage the stopping flange 58 of the adjusting shaft 26 with the catching face 48b.

The catching portion 48 is connected to the mounting plate 42 via a hinge 46 in the same way as the screw-in connecting portion 34 so as to enable conforming with a skeletal frame having a bulbous portion. Accordingly, the catching portion 48 can pivot with the hinge 46 as an axis so as to be supported at a desired angle on the mounting plate 42. A stopper 52 is also formed on the catching portion 48. Therefore, the catching portion 48 is restricted its pivoting range by the stopper 52. For example, pivoting of the catching portion 48 in a direction (i.e., backward) to approach the mounting plate 42 is restricted by the stopper 52. The catching portion 48 is formed so as to be able to stand upright on the mounting plate 42.

The adjusting shaft 26 to be extended through the lift plates 22 and 24 is provided with an adjusting area 54, on which a plurality of threads are formed, to be screwed into the screw hole 38 of the first lift plate 22. Further, the stopping flange 58 is formed on the end portion of the adjusting area 54 to externally protrude from its outer periphery.

On the other hand, an operation region 60 which is manipulated by an operator to operate the adjusting shaft 26 is formed at the rear end portion of the adjusting shaft 26. The operation region 60 is positioned outside of the patient's body to expand the bone. The shaft 26 is rotated by operating the operation region 60 so to increase or decrease the space between the first lift plate and the second lift plate.

An operation of the bone adjuster 20 of the first embodiment will be described with reference to FIG. 4 and FIG. 5. The bone adjuster 20, which can also be used to move linearly opposed bones in the same way as a conventional bone adjuster, will be described here in an example wherein opposed bone fragments 62, 64 are to be expanded in manner analogous to the opening of double doors.

Figure 2:
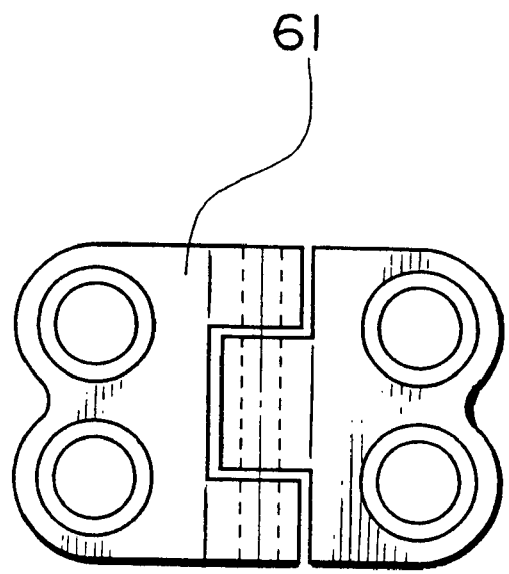
FIG. 2 is a plan diagram of a hinge plate of the first embodiment.
Figure 3:
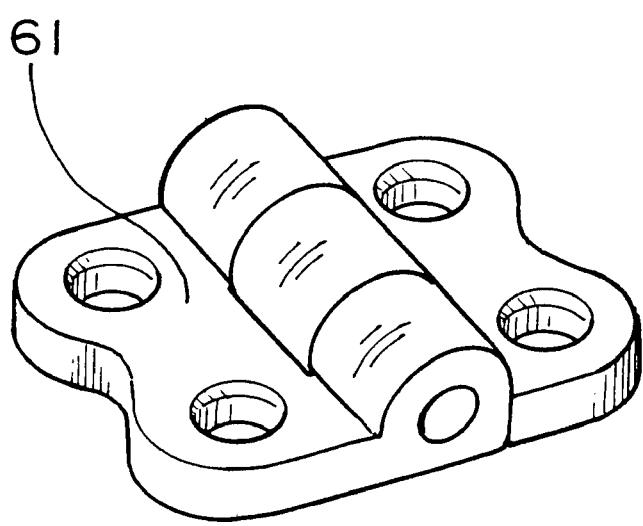
FIG. 3 is a perspective diagram of the hinge plate of the first embodiment.
Figure 4:
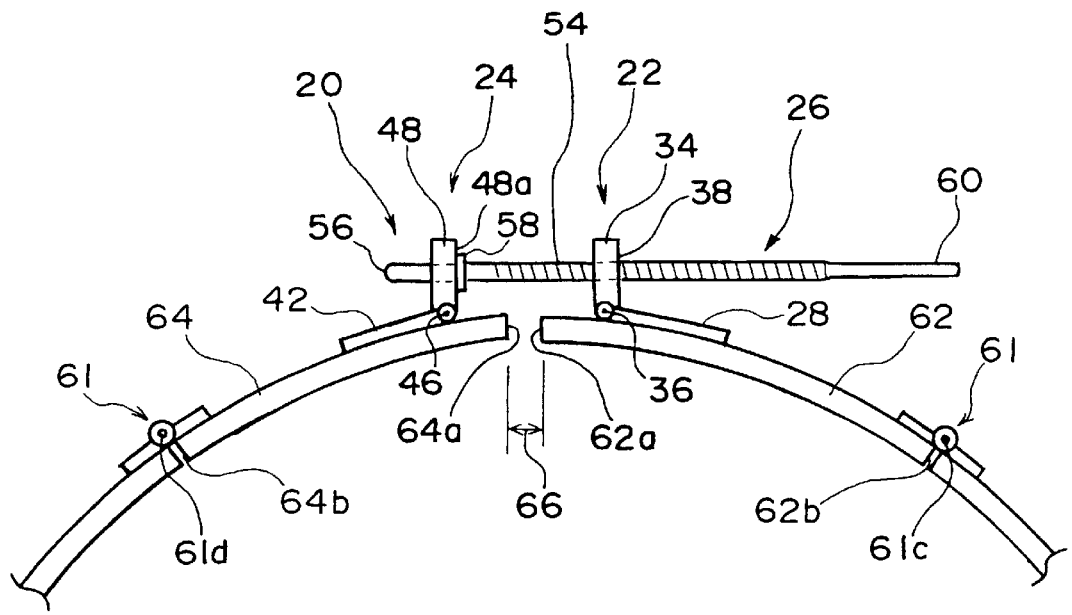
FIG. 4 is a diagram showing the bone adjuster of the first embodiment attached to bone fragments.
Figure 5:
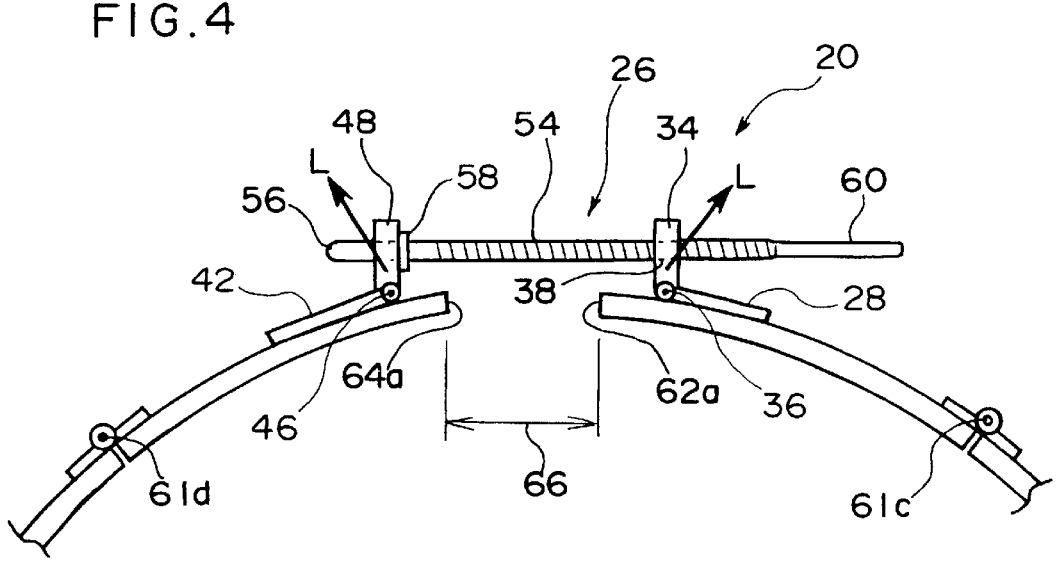
FIG. 5 is a diagram showing bone fragments being expanded by the bone adjuster of the first embodiment.

As shown in FIG. 4, to open the bone fragments 62 and 64 as if opening double doors to increase the space therebetween, it is first required that the bone fragments 62, 64 be independent bones, such as a jawbone. If not independent, the bone fragments 62, 64 are cut off at an appropriate position as shown in FIG. 4, and a hinge plate 61 shown in FIG. 2 and FIG. 3 is fixed to step over cut points 62b and 64b respectively. Thus, the bone fragments 62, 64 are cut and the hinge plates 61 are fixed, so that the bone fragments 62, 64 can have mutually opposed extension edges 62a, 64a which can be rotated around the hinge plate 61 as a fulcrum.

The bone adjuster 20 is then attached to the opposed bone fragments 62, 64. Specifically, the mounting plate 28 of the first lift plate 22 is bolted to the bone fragment 62 so to fasten the first lift plate 22. The adjusting shaft 26 is then inserted from its operation region 60 into the screw hole 38 of the fastened first lift plate 22 and screwed into the neighborhood of the stopping flange 58 of the screw area 54.

The second lift plate 24 is positioned so as to oppose the first lift plate 22 with its mounting plate 42 bolted to the bone fragment 64. After fixing the second lift plate 24 to the bone fragment 64, the operation region 60 of the adjusting shaft 26 is operated to insert the end 56 of the adjusting shaft 26 into the holding hole 50 of the catching portion 48 so to engage the stopping flange 58 with the inside face of the catching portion 48.

After attaching the bone adjuster 20, the process of bone expansion is begun. As shown in FIG. 5, bone lengthening is performed by gradually operating the operation region 60 of the adjusting shaft 26 to apply a force to expand the space between the lift plates 22 and 24. More specifically, the catching portion 48 is limited its backward pivot by the stopper 52, so that when the inside catching surface 48a of the catching portion 48 is pushed by the stopping flange 58 of the adjusting shaft 26, the additional force is applied to each of the hinge plates 22, 24 to expand the space between the bone fragments 62, 64.

However, the bone fragments 62, 64 are restricted by surrounding bones and are not free to slide in the direction (substantially a horizontal direction in FIG. 5) that the force is applied. Therefore, the extension edges 62a, 64a of the bone fragments 62, 64 are lifted up with hinges 61c, 61d of the hinge plates as a fulcrum as if doors are opened.

The upward movement of the bone fragments 62, 64 can be made as the hinge plates 22, 24 are provided with the hinges 36, 46. Specifically, the screw-in connecting portion 34 is tilted with the hinge 36 as a fulcrum to move away from the mounting plate 28 in correspondence with the movement of the bone fragments 62, 64. The catching portion 48 is also tilted in the same way with the hinge 46 as a fulcrum to move away from the mounting plate 42.

Specifically, when the bone fragments 62, 64 are opened in this manner and inclined, the screw-in connecting portion 34 and the catching portion 48 are inclined in an opposite direction to counteract the inclination of the bone fragments. By maintaining a parallel state, the adjusting shaft 26 can be supported appropriately by virtue of the screw-in connecting portion 34 and the catching portion 48.

The screw-in connecting portion 34 and the catching portion 48 are erected upright in the vicinity of the tops of the elevated bone fragments 62, 64 when the space between the extension edges 62a and 64a of the bone fragments 62, 64 is increased by the adjusting shaft 26, again as if double doors are opened. In this state, the adjusting shaft 26 is further operated, and the force applied to the lift plates is additionally applied to the extension edges 62a, 64a of the bone fragments 62, 64 than the one applied initially. Thus, the force in direction L to lift the extension edges 62a, 64a is further increased. Therefore, it is possible to expand the space between the bone fragments 62, 64 while maintaining a protrusion between them.

Figure 6:
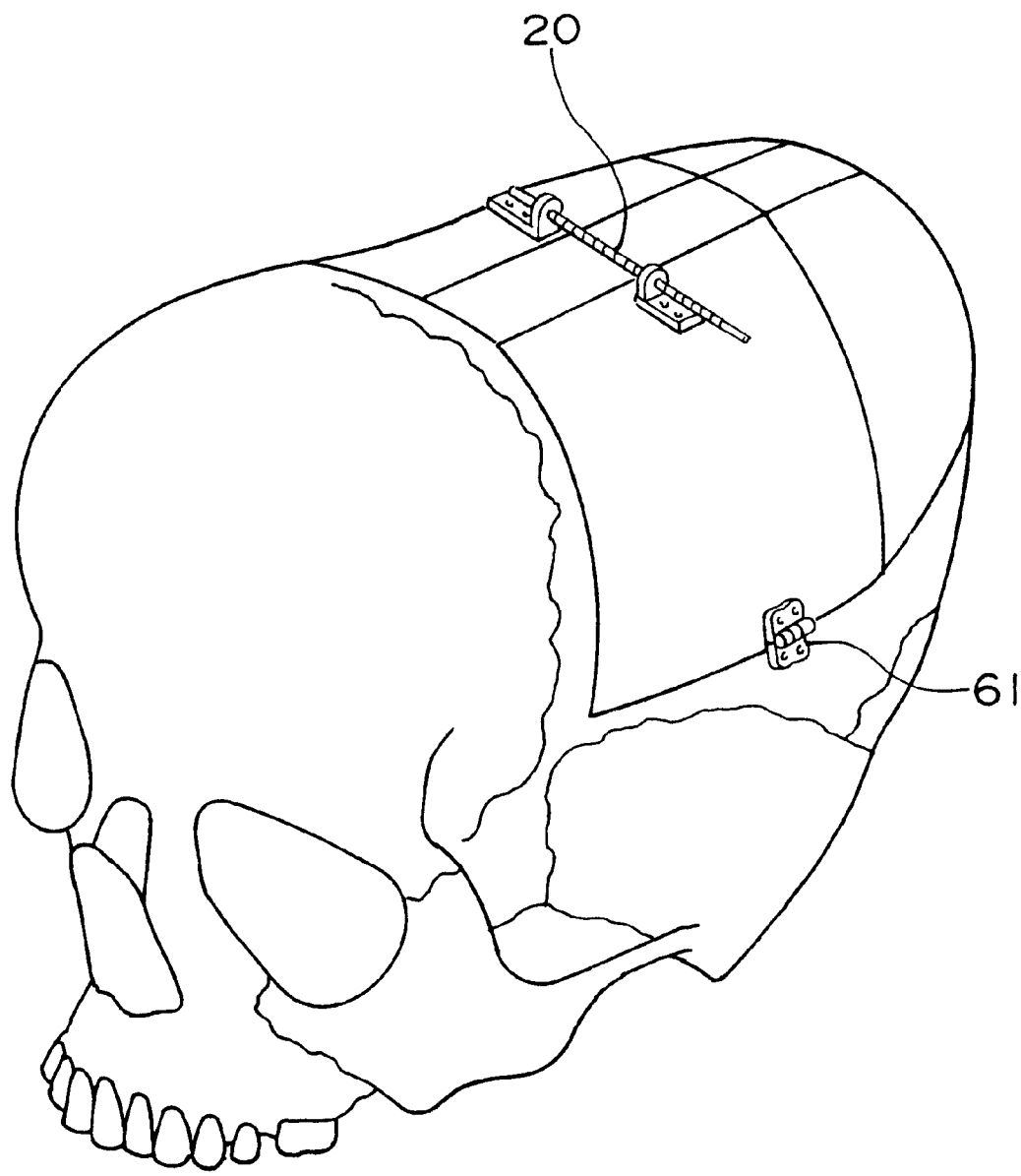
FIG. 6 is a diagram showing an example in which bone fragments of a skull area are expanded by the bone adjuster of the present invention.

Thus, the bone adjuster 20 enables expansion of the space between the extension edges 62a, 64a by spreading the bone fragments 62, 64 as described above. New bone is then able to grow from the extension edges 62a, 64a of the bone fragments 62, 64 so to fill a space 66 formed between the bone fragments 62, 64. The bone adjuster 20 can adjust a round skeletal frame such as the skull as shown in FIG. 6 to conform with its roundness.

Although in the above example, the bone adjuster 20 was used to expand the bone, it is to be understood that the bone adjuster 20 can also be used for compression of the bone. For compression of the bone, an enlarged bone is cut off at a certain point, and the bone adjuster 20 is fastened to bridge the cut bone fragments.

Figure 7:
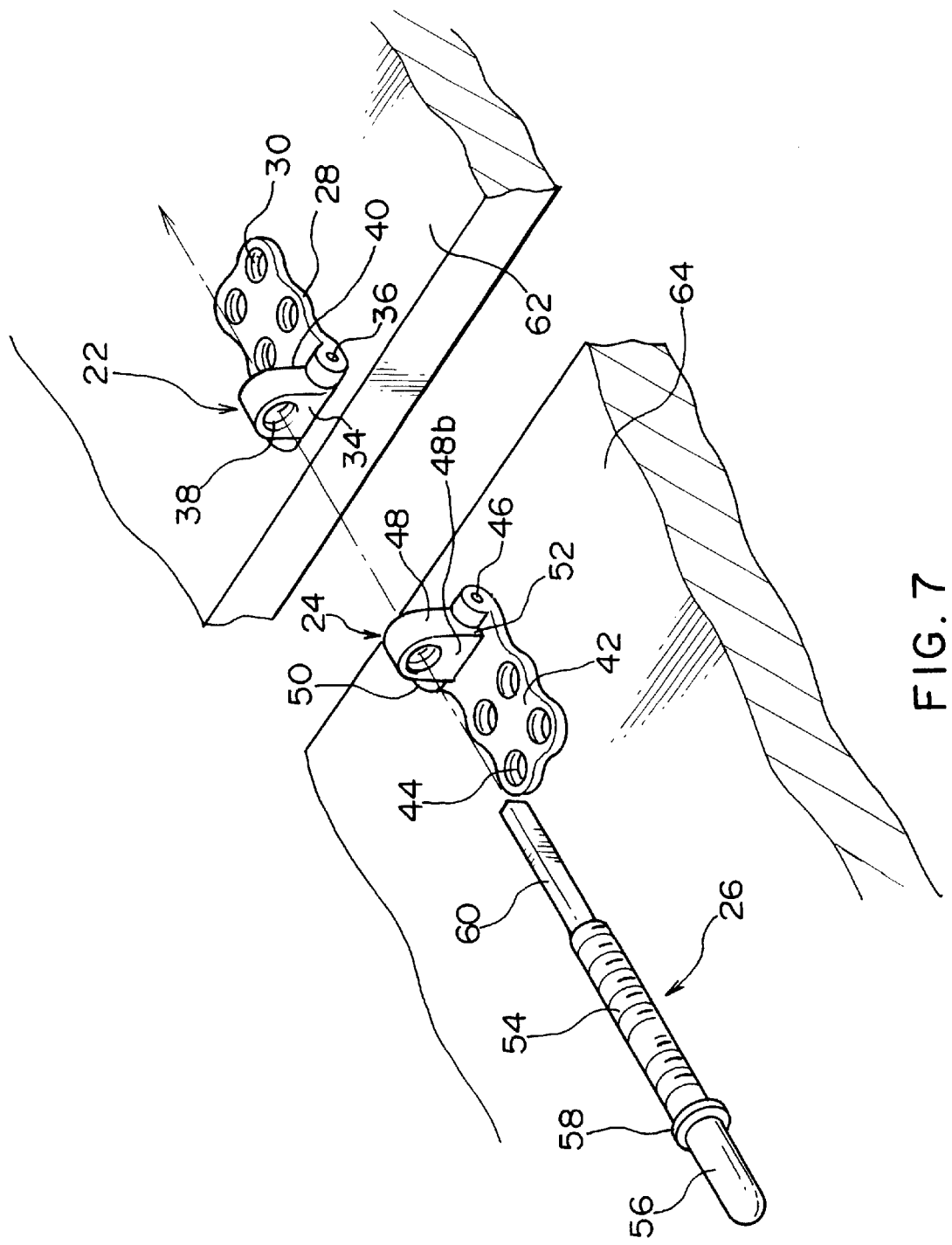
FIG. 7 is a diagram showing an example wherein the bone adjuster of the first embodiment is fastened to decrease a space between bone fragments.

As shown in FIG. 7, the first lift plate 22 is fastened to the bone fragment 62 and the second lift plate 24 is fastened to the bone fragment 64. The adjusting shaft 26 is inserted into the catching hole 50 of the catching portion 48 of the second lift plate 24 to extend through the lift plates 22 and 24, so that the stopping flange 58 of the adjusting shaft 26 is engaged with the outside catching surface 48b of the catching portion 48 of the second lift plate 24. The adjusting shaft 26 is then operated in this state to apply a force to decrease the space between the lift plates 22 and 24 so to decrease the space between the opposed bone fragments 62 and 64, thereby reducing the bone. When the bone size is decreased, it is possible to flatten an enlarged or swollen bone by reversing appropriate steps of the procedure for distraction of the bone.

Second Embodiment

Figure 8:
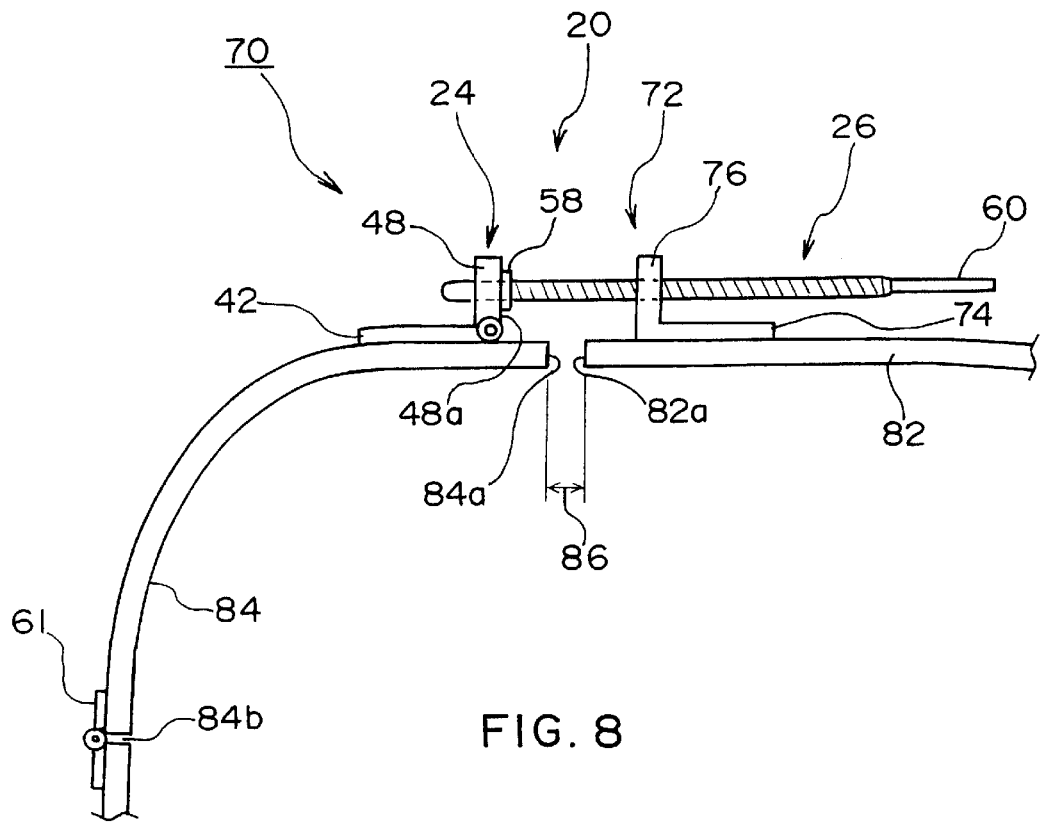
FIG. 8 is a diagram showing the bone adjuster of a second embodiment fastened to bone fragments.

FIG. 8 shows a bone adjuster 70 according to a second embodiment of the present invention. While in the first embodiment a screw-in connecting portion and a catching portion were pivotably connected to the mounting plate with the hinge as the axis, in this second embodiment, only the catching portion is pivotably connected to the mounting plate via the hinge, and the screw-in connecting portion is fixed to the mounting plate at a given angle. Identical reference numerals as those used above will be used to designate identical or corresponding parts, and their descriptions will not be repeated.

In FIG. 8, a screw-in connecting portion 76 is fixed to a mounting plate 74 of a first lift plate 72 at a given angle. Thus, the screw-in connecting portion 76 is structured in the same way as the screw-in connecting portion 34 (FIG. 1) of the first embodiment, except that the screw-in connecting portion 76 is fixed to the mounting plate 74 at the given angle. In the screw-in connecting portion 76 is also formed a screw hole into which the adjustment shaft 26 can be inserted.

In FIG. 8, the screw-in connecting portion 76 is fixed to the mounting plate 74 at a right angle, but this angle can be determined in accordance with the shape of a bone fragment to which the bone adjuster is applied.

Next, an example operation of the bone adjuster 70 will be described. The bone lengthening instrument 70 of this embodiment can linearly expand or contract mutually opposed bone fragments, but this example will describe a case of opening a bone fragment 84, which is one of mutually opposed bone fragments, as if opening a single swing door. The bone fragment 84 to be opened is an independent bone fragment such as a jawbone. If the bone fragment 84 is not independent, it is cut off, and the hinge plate 61 is fastened to step over a cut-off portion 84b.

In FIG. 8, the mounting plate 74 of the first lift plate 72 is fixed to the bone fragment 82 in the vicinity of its extension edge 82a. The adjusting shaft 26 is screwed through the first lift plate 72.

On the other hand, the mounting plate 42 of the second lift plate 24 is fastened to an opposing bone fragment 84 in the vicinity of its extension edge 84a so as to oppose the first lift plate 72. Then, the stopping flange 58 of the adjusting shaft 26 is engaged with the inside face 48a of the catching portion 48 of the second lift plate 24 to complete the fastening of the bone adjuster 70.

Figure 9:
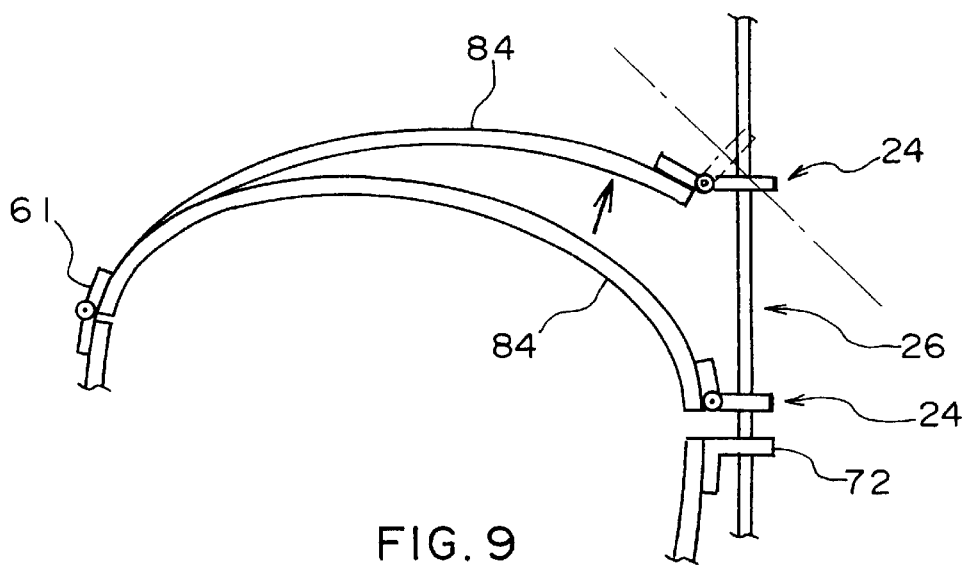
FIG. 9 is a schematic diagram showing bone lengthening by the bone adjuster of the second embodiment.

To adjust the bone, the adjusting shaft 26 is operated to apply a force to expand the space between the lift plates 72 and 74. The expanding force acts to expand the bone fragments 82 and 84, and the bone fragment 84 provided with the hinge plate 61 is moved with the hinge plate 61 as a fulcrum, as if a single swinging door is opened, because the bone fragments 82, 84 cannot slide in a straight line. The described operation is schematically shown in FIG. 9.

Thus, the bone adjuster 70 of this embodiment enables moving the bone fragment 84 as described above in order to form a space 86 between the bone fragments 82 and 84.

Figure 10:
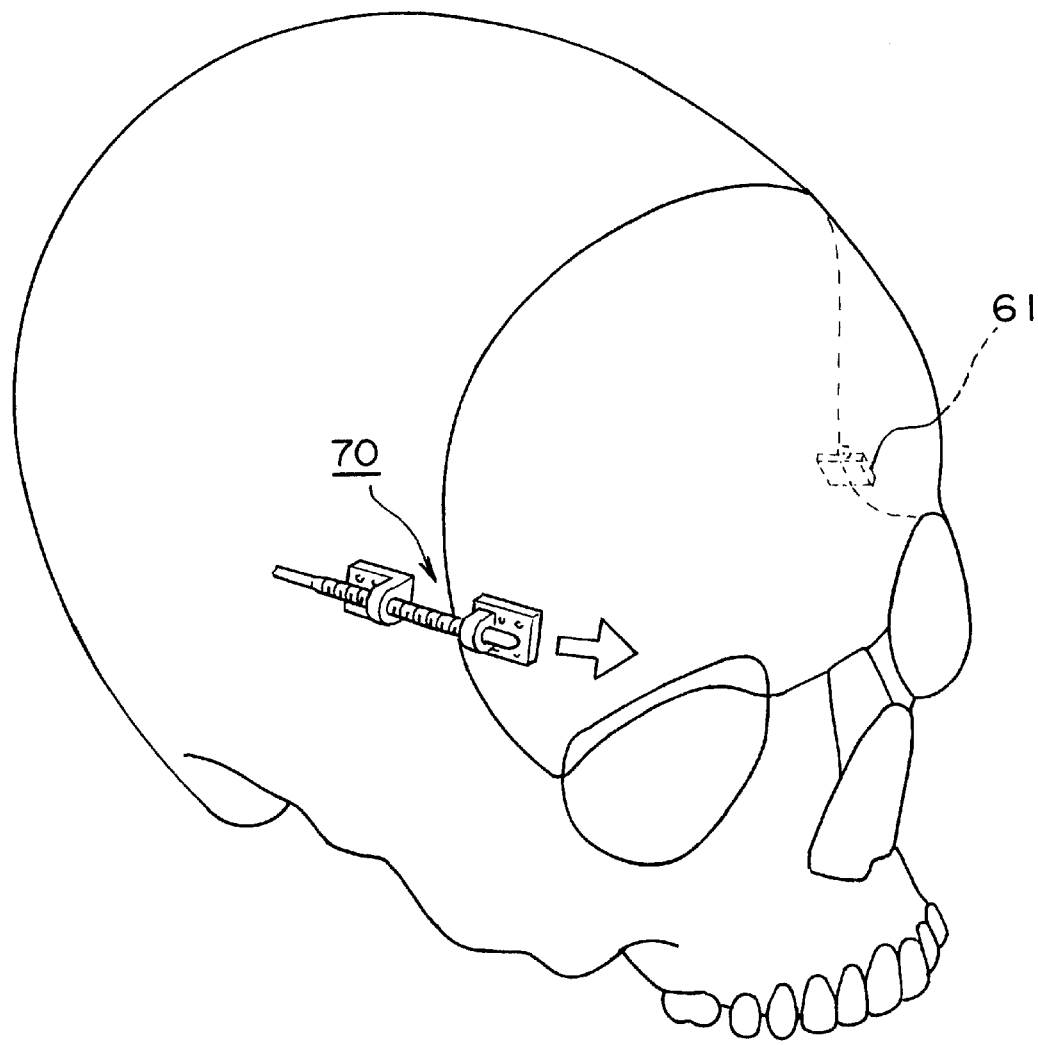
FIG. 10 is a diagram showing an example wherein a bone segment of skull, jaw, and face areas is adjusted by the bone adjuster of the second embodiment.

Bone is then able to grow from the expansion edges 82*a*, 84*a* of the bone fragments to fill the space 86, and formation of bone in an appropriately curved shape can be promoted. Therefore, the bone lengthening instrument of this embodiment can be used to compensate a depressed fracture or the like of a part (e.g., a forehead) of facial bones, as shown in FIG. 10 for example.

While the bone adjuster of this embodiment was used for distraction of the bone, it can also be used for compression of the bone in the same way as in the first embodiment.

An illustrative bone adjuster with a hinge provided on one lift plate was described in the above embodiment. This same operation, as if opening a single swinging door, can also be made by the bone lengthening instrument of the first embodiment. For example, when a bone fragment to be moved as if opening a single swing door is not independent, it is cut off and provided with the hinge plate 61 on the cut-off part. Thus, the bone lengthening instrument 20 of the first embodiment can be used in the same way.

Third Embodiment

As described above, the bone adjuster can be operated to move the bone fragments as if opening or closing a door in a different way from the conventional bone adjuster. Especially, when the bone fragments are moved as if opening a door, a large load is applied to the front, namely the hinge, of the lift plate. For some applications, it is necessary to improve a fixing strength of the lift plate against the bone fragment so to withstand the load.

Figure 11:
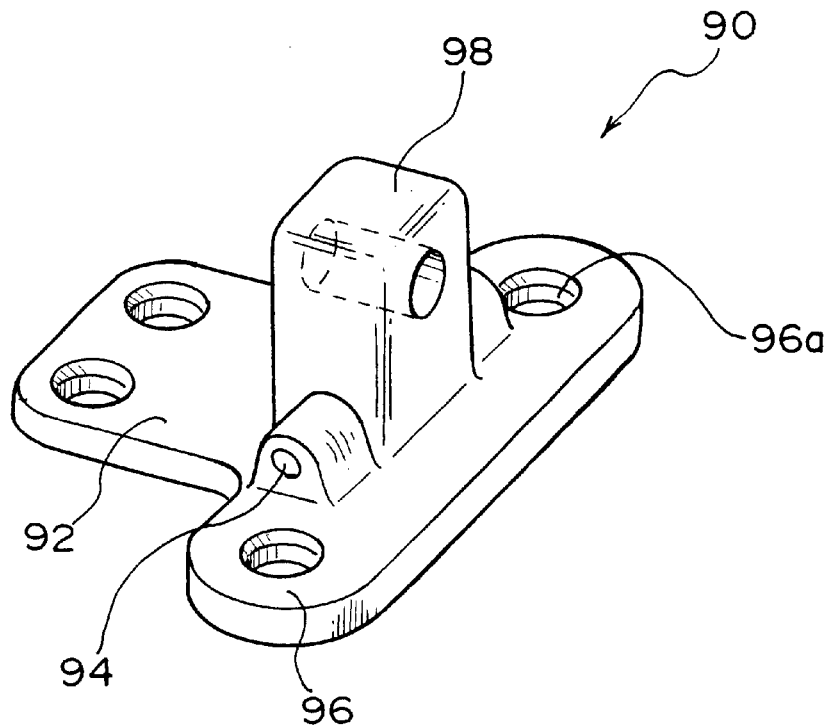
FIG. 11 is a diagram showing another embodiment of a first lift plate.
Figure 12:
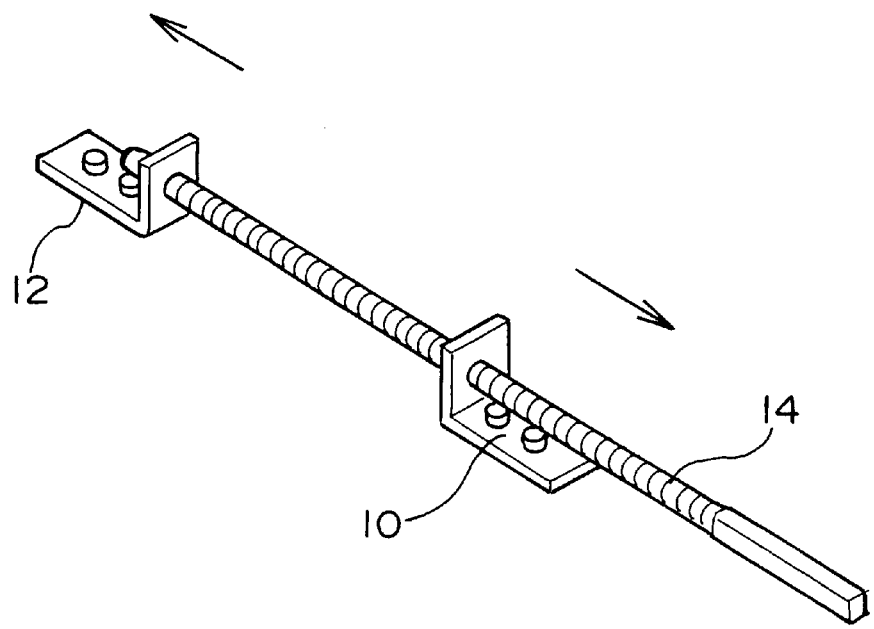
FIG. 12 is a perspective diagram showing a conventional bone lengthening instrument.

FIG. 11 shows a first lift plate 90 with augmented fixing strength. The first lift plate 90 shown in FIG. 11 is provided with a mounting plate 92 and also a reinforcing plate 96 with a hinge 94 between them.

This reinforcing plate 96 is not restricted to a particular shape as far as it can enhance a fixing strength of the first lift plate 90. For example, it can be formed to protrude horizontally, and bolt holes 96*a* can be formed without hindering the position where the adjusting shaft is mounted as shown in FIG. 11. By configuring the invention in this way, the lift plate can be fastened to the bone fragment with the adjusting shaft mounted on it.

The lift plate provided with the aforesaid reinforcing plate has increased fixing force against the bone fragment, and, when the adjusting shaft is operated, a pushing force applied to a screw-in connecting portion 98 and the like can be transmitted efficiently to the entire plate and also to the bone fragment. A reinforcing plate formed on the first lift plate was described above as an example of the third embodiment of the present invention, but such a reinforcing plate can also be formed on the second lift plate in the same way to improve its fixing force to the bone fragment so to enable an efficient bone adjustment.

As described above, the present invention can be used to adjust any type of skeletal frames, from a bone fragment having a swelled shape to a flat skeletal frame, and the adjustment is not limited to the distraction of a bone, but can also be used for compression of the bone.

While there have been described that what are at present considered to be preferred embodiments of the invention, it is to be understood that various modifications may be made thereto, and it is intended that the appended claims cover all such modifications as fall within the true spirit and scope of the invention.

What is claimed is:

1. A bone adjuster comprising a first lift plate for fastening to one bone fragment, a second lift plate for fastening to another bone fragment, and an adjusting shaft which is screwed through the first lift plate and has its leading end engaged with the second lift plate, the adjusting shaft being rotated to adjust a distance between both the lift plates so to adjust a space between the opposed bone fragments, wherein:

the first lift plate is provided with a first mounting plate to be fastened to one of the bone fragments and a screw-in connecting portion which is connected to the first mounting plate and in which the adjusting shaft is screwed;

the second lift plate is provided with a second mounting plate to be fastened to the other bone fragment and a catching portion which is connected to the second mounting plate and holds the leading end of the adjusting shaft; and at least the catching portion is connected to the second mounting plate via a hinge.

2. The bone adjuster according to claim 1, wherein both the screw-in connecting portion and the catching portion are pivotably connected to the first mounting plate and the second mounting plate via a hinge respectively.

3. The bone adjuster according to claim 1, wherein a stopping flange is formed on the end portion of the adjusting shaft so as to externally protrude from its outer periphery, the catching portion comprises a catching plate having a catching surface to engage with the stopping flange, and the catching plate is formed a holding hole in which the end of the adjusting shaft is inserted and held.

4. The bone adjuster according to claim 2, wherein a stopping flange is formed on the end portion of the adjusting shaft so as to externally protrude from its outer periphery, the catching portion comprises a catching plate having a catching surface to engage with the stopping flange, and the catching plate is formed with a holding hole into which one end of the adjusting shaft is inserted and held.

5. The bone adjuster according to claim 1, wherein the catching portion is further provided with a stopper to restrict the catching portion to pivot within a given range.

6. The bone adjuster according to claim 2, wherein the screw-in connecting portion and the catching portion are further provided with a stopper to restrict the screw-in connecting portion and the catching portion to pivot within a given range.

7. The bone adjuster according to claim 3, wherein the catching plate has:

an inside catching surface on the opposite side of the screw-in connecting portion to engage with the stopping flange so to expand the space between the bone fragments; and an outside catching surface on the other side of the inside catching surface to engage with the stopping flange so to decrease the space between the bone fragments.

8. The bone adjuster according to claim 4, wherein the catching plate has:

an inside catching surface on the opposite side of the screw-in connecting portion to engage with the stopping flange so to expand the space between the bone fragments; and an outside catching surface on the other side of the inside catching surface to engage with the stopping flange so to decrease the space between the bone fragments.

9. The bone adjuster according to claim 1, further comprising a hinge plate which is used, when at least one of the bone fragments is cut off at an appropriate point, to connect the cut-off ends so to enable at least one of the cut-off ends to pivot.

10. The bone adjuster according to claim 2, further comprising a hinge plate which is used, when at least one of the bone fragments is cut off at an appropriate point, to connect the cut-off ends so to enable at least one of the cut-off ends to pivot.

11. The bone adjuster according to claim 1, wherein at least one of the first lift plate and the second lift plate is provided with a reinforcing plate, the hinge is situated between the reinforcing plate and the respective mounting plate, and the reinforcing plate is provided with a fixing section to be fixed to a bone fragment.

12. The bone adjuster according to claim 2, wherein at least one of the first lift plate and the second lift plate is provided with a reinforcing plate, the hinge is situated between the reinforcing plate and the respective mounting plate, and the reinforcing plate is provided with a fixing section to be fixed to a bone fragment.

13. The bone adjuster according to claim 1, wherein the bone adjuster is formed of a material having little effect on the human body.

14. The bone adjuster according to claim 2, wherein the bone adjuster is formed of a material having little effect on the human body.

15. The bone adjuster according to claim 9, wherein the bone adjuster is formed of a material having little effect on the human body.

16. The bone adjuster according to claim 10, wherein the bone adjuster is formed of a material having little effect on the human body.

17. The bone adjuster according to claim 11, wherein the bone adjuster is formed of a material having little effect on the human body.

18. The bone adjuster according to claim 12, wherein the bone adjuster is formed of a material having little effect on the human body.

* * * * *